United States Patent
Komazaki et al.

(10) Patent No.: US 9,841,546 B2
(45) Date of Patent: Dec. 12, 2017

(54) LIGHT SOURCE APPARATUS

(71) Applicant: OLYMPUS CORPORATION, Tokyo (JP)

(72) Inventors: Iwao Komazaki, Saitama (JP); Takeshi Ito, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 395 days.

(21) Appl. No.: 14/553,083

(22) Filed: Nov. 25, 2014

(65) Prior Publication Data
US 2015/0078031 A1 Mar. 19, 2015

Related U.S. Application Data

(63) Continuation of application No. PCT/JP2013/057870, filed on Mar. 19, 2013.

(30) Foreign Application Priority Data

May 28, 2012 (JP) ................................. 2012-121139

(51) Int. Cl.
*F21S 4/00* (2016.01)
*F21V 8/00* (2006.01)
(Continued)

(52) U.S. Cl.
CPC ........ *G02B 6/0008* (2013.01); *A61B 1/00096* (2013.01); *A61B 1/00101* (2013.01); *A61B 1/0653* (2013.01); *F21K 9/61* (2016.08); *F21K 9/64* (2016.08); *G02B 19/0019* (2013.01); *G02B 19/0023* (2013.01); *G02B 19/0052* (2013.01); *G02B 23/2423* (2013.01); *G02B 23/2469* (2013.01); *G02B 23/2476* (2013.01); *G02B 6/04* (2013.01)

(58) Field of Classification Search
CPC .. A61B 1/00101; A61B 1/0653; G02B 6/0008
See application file for complete search history.

(56) References Cited

U.S. PATENT DOCUMENTS 5,989,185 A * 11/1999 Miyazaki ........... A61B 1/00096
348/E7.085
2007/0213592 A1* 9/2007 Yamada ............. A61B 1/00096
600/178

(Continued)

FOREIGN PATENT DOCUMENTS

JP 2005-323737 A 11/2005
JP 2009-043668 A 2/2009
(Continued)

OTHER PUBLICATIONS

International Search Report dated Apr. 23, 2013 issued in PCT/JP2013/057870.
(Continued)

*Primary Examiner* — Evan Dzierzynski
(74) *Attorney, Agent, or Firm* — Scully, Scott, Murphy & Presser, P.C.

(57) ABSTRACT

A light source apparatus includes an optical illumination unit that converts optical characteristics of primary light emitted from a light source unit and emits secondary light different from the primary light; and an adapter unit that outwardly emits illumination light generated based on the secondary light emitted from the optical illumination unit and that is attachable to/detachable from the optical illumination unit. A radiation angle control member converts a traveling direction of the secondary light so that the secondary light allowed to emit from a light conversion member toward the radiation angle control member in the secondary light allowed to emit from the light conversion member travels toward the adapter unit through the secondary light emit portion.

20 Claims, 9 Drawing Sheets

(51) Int. Cl.
*A61B 1/06* (2006.01)
*A61B 1/00* (2006.01)
*G02B 19/00* (2006.01)
*G02B 23/24* (2006.01)
*F21K 9/61* (2016.01)
*F21K 9/64* (2016.01)
*G02B 6/04* (2006.01)

(56) References Cited

U.S. PATENT DOCUMENTS

2009/0040598 A1\* 2/2009 Ito .................. A61B 1/0638
 359/332
2010/0080016 A1\* 4/2010 Fukui ............... A61B 1/0653
 362/574

FOREIGN PATENT DOCUMENTS

| JP | 4370199 B2 | 11/2009 |
| JP | 2010-081957 A | 4/2010 |
| JP | 2010-199027 A | 9/2010 |
| JP | 2011-072424 A | 4/2011 |

OTHER PUBLICATIONS

Japanese Office Action dated Nov. 22, 2016 in related Japanese Patent Application No. 2012-121139.
International Preliminary Report on Patentability together with the Written Opinion dated Dec. 11, 2014 from related International Application No. PCT/JP2013/057870, together with an English language translation.

\* cited by examiner

US 9,841,546 B2

LIGHT SOURCE APPARATUS

CROSS-REFERENCE TO RELATED APPLICATIONS

This application is a Continuation application of PCT Application No. PCT/JP2013/057870, filed Mar. 19, 2013 and based upon and claiming the benefit of priority from prior Japanese Patent Application No. 2012-121139, filed May 28, 2012, the entire contents of all of which are incorporated herein by reference.

BACKGROUND OF THE INVENTION

1. Field of the Invention

The present invention relates to a light source apparatus having an illumination unit and an adapter unit that is attachable to/detachable from this illumination unit.

2. Description of the Related Art

For example, Japanese Patent No. 4370199 discloses an endoscope apparatus. This endoscope apparatus has, e.g., a light source unit that emits light having a specific wavelength and an inserting section that guides the light emitted from the light source unit. Further, this endoscope apparatus also has a diffusion optical member that is arranged at a distal end portion of the inserting section that is an optical illumination unit and diffuses and emits light frontward, and an adapter unit that is attachable to/detachable from the distal end portion of the inserting section.

The light source unit has a light source section that emits light having a specific wavelength, e.g., 450 nm or less and a light focusing member that focuses the light emitted from the light source section. The light source section has, e.g., laser diodes that emit laser beams that are excitation lights.

The inserting section has a light guide that guides the light to the distal end portion of the inserting section. This light is emitted from a laser light source and focused by the light focusing member. The light guide is formed of, e.g., an optical fiber. The light guide has an emit end portion arranged at the distal end portion of the inserting section.

The diffusion optical member is arranged at the distal end portion of the inserting section to face the emit end portion of the light guide. The diffusion optical member has, e.g., a diffusion lens. The distal end portion of the inserting section including the diffusion optical member is included in the optical illumination unit.

The adapter unit is attached to the distal end portion of the inserting section to cover a front face of the distal end portion of the inserting section. The adapter unit holds a discoid fluorescent substance that emits light having a wavelength different from a wavelength of the light emitted from the light source section based on this light. The fluorescent substance is a wavelength conversion member and also an optical member.

The adapter unit has a front face plate arranged on a front face of the adapter unit. The front face plate has an illumination window that faces the diffusion optical member and the fluorescent substance arranged in the entire illumination window. Furthermore, the front face plate has a cylindrical reflection member that is a mirror surface that is arranged on an entire inner peripheral surface of the illumination window and on the diffusion optical member side to the fluorescent substance. The reflection member is a diffusion prevention member that prevents diffusion of light. An inner diameter of the reflection member is substantially equal to an outer diameter of the diffusion optical member or larger than the outer diameter of the diffusion optical member.

When the fluorescent substance is irradiated with a laser beam, it emits light including light of a wavelength of substantially 400 nm to substantially 650 nm frontward. This light is, e.g., white light.

In the endoscope apparatus, the adapter unit having the fluorescent substance is attachable to/detachable from the distal end portion of the inserting section in the optical illumination unit. Therefore, emission of the light of 450 nm or less and emission of the white light are easily changed over by attachment/detachment of the adapter unit. In other words, when the adapter unit is detached, the light emitted from the light source section is diffused by the diffusion optical member and allowed to emit as diffusion light. Furthermore, when the adapter unit is attached, substantially all of the diffused light is focused to the fluorescent substance by the reflection member and transmitted through the fluorescent substance. At this time, the diffused light is turned to the white light and allowed to emit by the fluorescent substance.

As described above, in Japanese Patent No. 4370199, substantially all of the diffused light is guided to the fluorescent substance by the reflection member. However, Japanese Patent No. 4370199 does not disclose a configuration for a light guide. Specifically, a beam divergence angle of the diffused light emitting from the diffusion optical member and an optical connection configuration of the diffusion optical member and the reflection member are not disclosed.

Therefore, there is a concern that the light is not efficiently guided from the optical illumination unit to the adapter unit.

In view of the above-described circumstances, it is an object of the present invention to provide a light source apparatus that can efficiently guide light from an optical illumination unit to an adapter unit.

BRIEF SUMMARY OF THE INVENTION

An aspect of a light source apparatus including a light source unit that emits primary light; an optical illumination unit that converts optical characteristics of the primary light emitted from the light source unit and emits secondary light different from the primary light; and an adapter unit that outwardly emits illumination light generated based on the secondary light emitted from the optical illumination unit and that is attachable to/detachable from the optical illumination unit, wherein a central axis of the primary light emitted from the light source unit is called a light axis, in the light axis direction, the optical illumination unit side is called a rear side, the adapter unit side is called a front side, and a direction orthogonal to the light axis is called a lateral side, the optical illumination unit comprises: a light conversion member that converts the optical characteristics of the primary light and generates the secondary light different from the primary light; a secondary light emit portion that is arranged in the front side to the light conversion member and allows the secondary light to emit to the outside of the optical illumination unit; and a radiation angle control member that controls a radiation angle of the secondary light allowed to emit to the outside of the optical illumination unit, the adapter unit comprises: an adapter unit side incident portion which is optically connected to the secondary light emit portion and from which the secondary light allowed to emit from the secondary light emit portion enters; and an adapter unit side emit portion that allows the illumination light to emit toward the outside, and the radiation angle control member converts a traveling direction of the secondary light so that the secondary light allowed to emit from the light conversion member toward the radiation angle control member in the secondary light allowed to emit from the light conversion member travels toward the adapter unit through the secondary light emit portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1A:
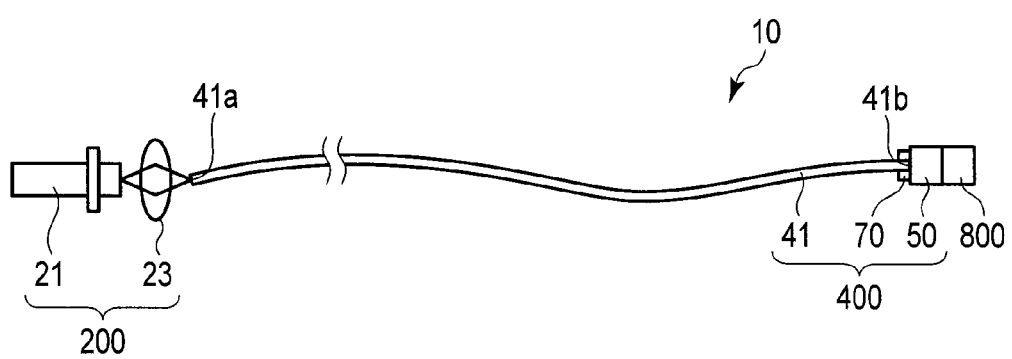
FIG. 1A is a schematic view of a light source apparatus according to a first embodiment of the present invention.

An embodiment according to the present invention will now be described hereinafter with reference to the drawings.

First Embodiment

[Configuration]

A first embodiment will now be described with reference to FIG. 1A, FIG. 1B, FIG. 1C, and FIG. 1D. It is to be noted that a central axis of primary light emitting from an emit portion 41b of a light source unit 200 will be referred to as a light axis 11 hereinafter.

Moreover, in a direction of the light axis 11, an optical illumination unit 400 side will be referred to as a rear side, an adapter unit 800 side will be referred to as a front side, and a direction orthogonal to the light axis 11 will be referred to as a lateral side.

[Configuration of Light Source Apparatus 10]

Figure 1B:
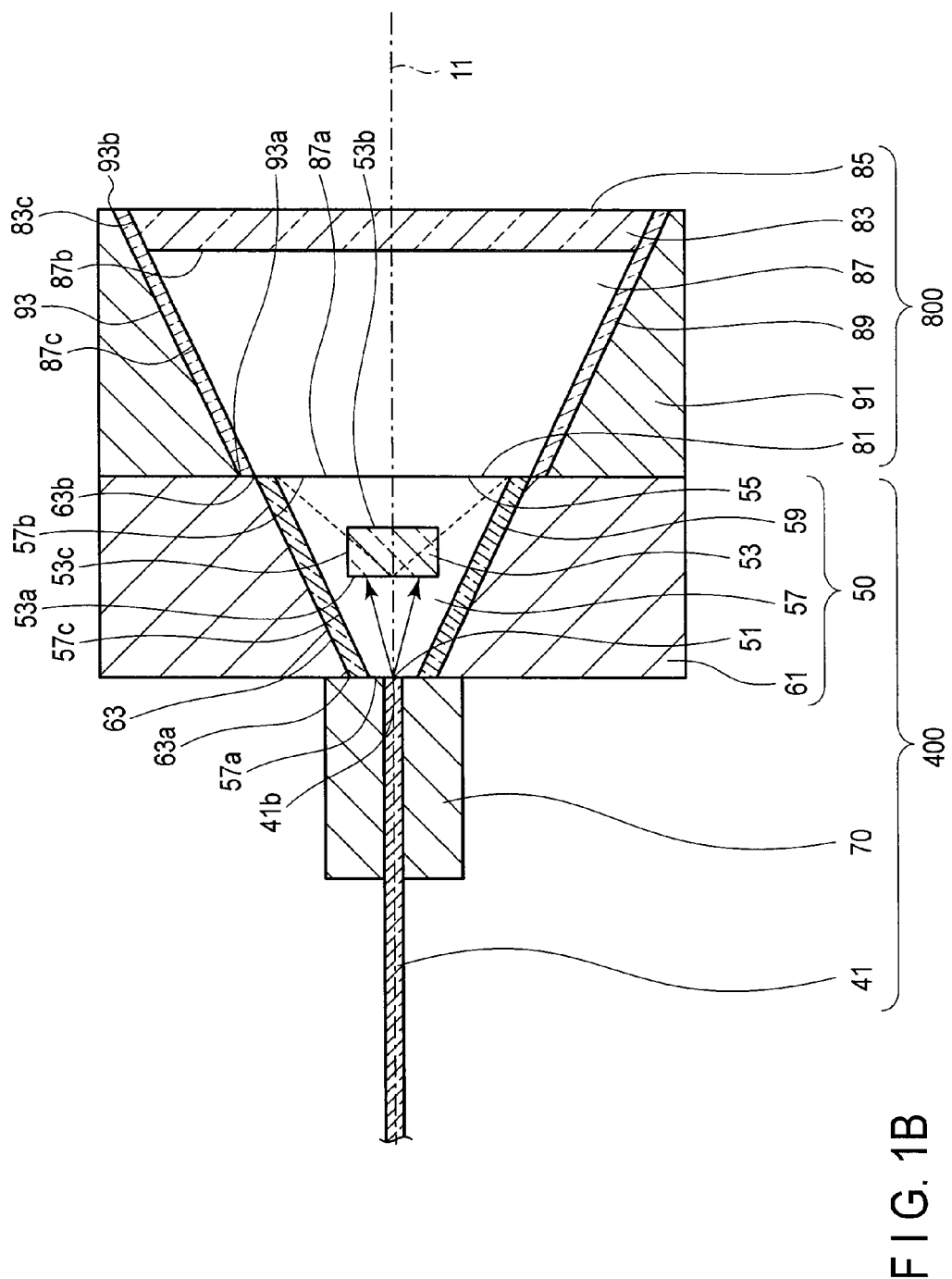
FIG. 1B is a view showing an optical configuration of an optical illumination unit and an adapter unit where the adapter unit is attached to the optical illumination unit.
Figure 1C:
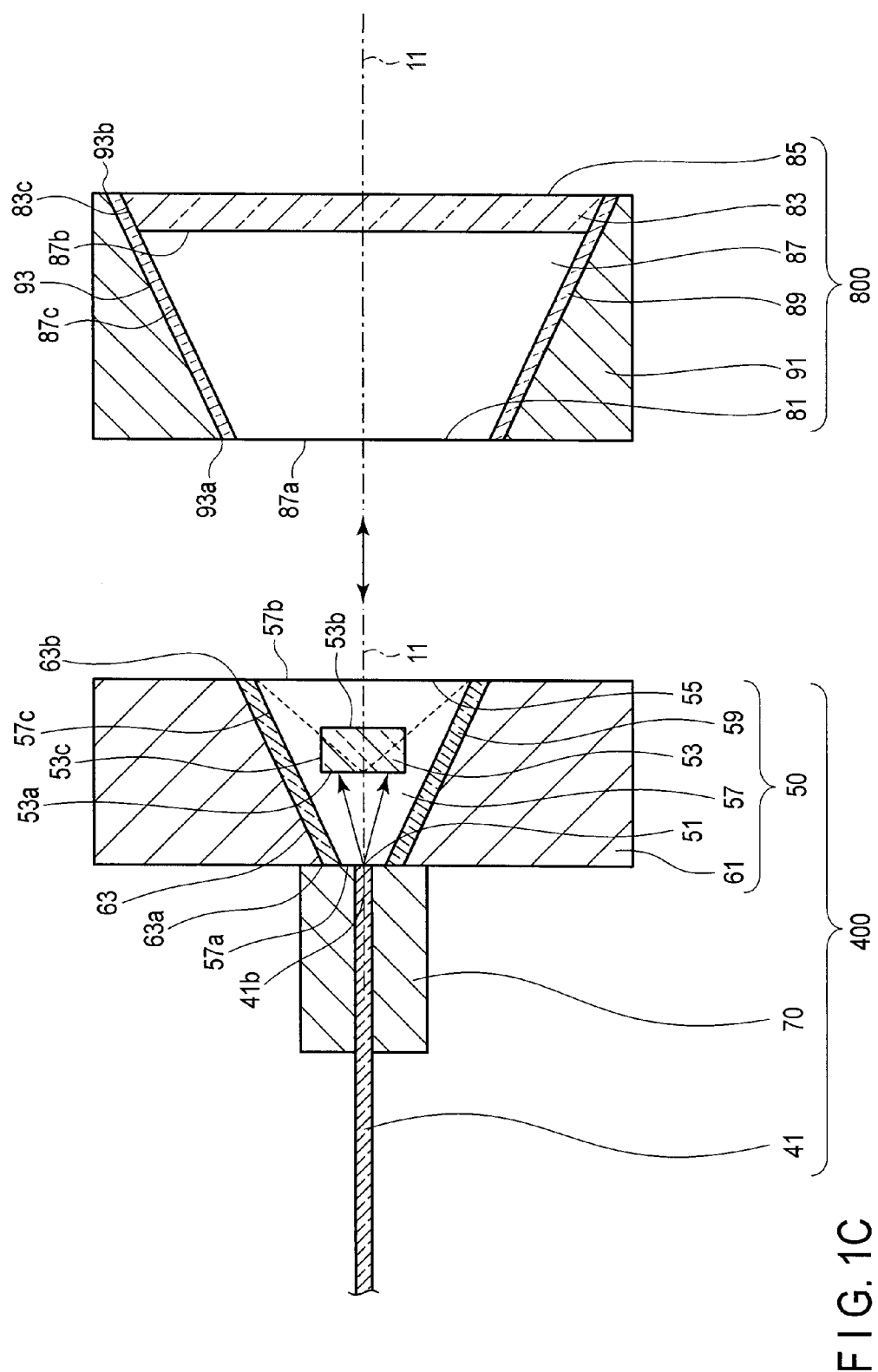
FIG. 1C is a view showing a state that the adapter unit is detached from the optical illumination unit.

As shown in FIG. 1A, FIG. 1B, and FIG. 1C, a light source apparatus 10 has the light source unit 200 that emits the primary light, the optical illumination unit 400 that converts optical characteristics of the primary light emitted from the light source unit 200 and emits secondary light different from the primary light, and the adapter unit 800 that outwardly emits illumination light generated based on the secondary light emitted from the optical illumination unit 400 and that is attachable to/detachable from the optical illumination unit 400.

[Light Source Unit 200]

As shown in FIG. 1A, the light source unit 200 has a light source section 21 that emits the primary light and a lens 23 that focuses the primary light emitted from the light source section 21.

The light source section 21 has a semiconductor laser that emits the primary light. The primary light has a blue-violet laser beam whose wavelength is, e.g., approximately 400 nm.

[Optical Illumination Unit 400]

As shown in FIG. 1B, the optical illumination unit 400 has a light guide member 41 that guides the primary light emitted from the light source section 21 and an illumination unit 50 that converts the optical characteristics of the primary light guided by the light guide member 41 and emits the secondary light different from the primary light. Additionally, as shown in FIG. 1B, the optical illumination light 400 also has a holding member 70 that holds an emit portion 41b side of the light guide member 41 and mechanically connects the emit portion 41b side to the illumination unit 50 so that the emit portion 41b of the light guide member 41 can be optically connected to the illumination unit 50.

[Light Guide Member 41]

As shown in FIG. 1A, the light guide member 41 has, e.g., softness and flexibility, is bendable, and has an elongated columnar shape. The light guide member 41 has an incident portion 41a from which the primary light focused by the lens 23 enters and the emit portion 41b from which the primary light emits. The light guide member 41 guides the primary light from the incident portion 41a to the emit portion 41b.

The light guide member 41 has, e.g., an optical fiber. As this optical fiber, a multimode fiber having a numerical aperture Fna of approximately 0.22 and a core diameter of 50 μm is used. The primary light spreads with a beam divergence angle corresponding to this Fna and is allowed to emit from the emit portion 41b.

[Illumination Unit 50]

As shown in FIG. 1B, the illumination unit 50 has a primary light incident portion 51 which is optically connected to the emit portion 41b and from which the primary light allowed to emit from the emit portion 41b enters and a light conversion member 53 that is arranged away from the primary light incident portion 51, converts the optical characteristics of the primary light and thereby generates the secondary light different from the primary light when it is irradiated with the primary light that has entered from the primary light incident portion 51b. Further, as shown in FIG. 1B, the illumination unit 50 also has a secondary light emit portion 55 that is arranged in the front side to the light conversion member 53 and from which the secondary light is allowed to emit to the outside of the illumination unit 50.

Furthermore, as shown in FIG. 1B, the illumination unit 50 also has a light transmission member 57 that has the primary light incident portion 51 and the secondary light emit portion 55, is arranged between the primary light incident portion 51 and the light conversion member 53, and arranged to be at least partially continuous from the primary light incident portion 51 to the secondary light emit portion 55 so that the primary light and the secondary light can be transmitted there through.

Moreover, as shown in FIG. 1B, the illumination unit 50 also has a radiation angle control member 59 that is arranged on a peripheral surface 57c of the light transmission member 57 and controls a radiation angle of the secondary light emitted to the outside of the optical illumination unit 400 and a holding section 61 that holds the light transmission member 57 including the primary light incident portion 51, the light conversion member 53, the secondary light emit portion 55, and the radiation angle control member 59.

As shown in FIG. 1B, these members included in the illumination unit 50 and the holding member 70 have concentric shapes having the light axis 11 as a central axis, and they are rotation-symmetrically arranged with the light axis 11 at the center.

[Primary Light Incident Portion 51]

As shown in FIG. 1B, the primary light incident portion 51 is formed on part of a rear surface 57a of the light transmission member 57 on which the emit portion 41b abuts. In more detail, in the light transmission member 57, part of the rear surface 57a optically connected with the emit portion 41b is formed as the primary light incident portion 51. This rear surface 57a represents, e.g., a plane arranged on the rearmost side of the light transmission member 57 in the light axis 11 direction. The primary light incident portion 51 is arranged on the light axis 11 and formed on the central axis of the light transmission member 57. The primary light incident portion 51 has a shape and an area that are substantially equal to those of the emit portion 41b (a core diameter of the optical fiber). The primary light incident portion 51 is smaller than the secondary light emit portion 55.

[Light Conversion Member 53]

For example, the light conversion member 53 absorbs the primary light, converts light distribution characteristics of the absorbed primary light without changing its wavelength, and generates the secondary light having the converted light distribution characteristics. As described above, the light conversion member 53 is a light distribution conversion member that converts the light distribution of the primary light, and it is also an optical member that functions when it is irradiated with the primary light.

The light conversion member 53 faces the emit portion 41b and is arranged on the front side of the emit portion 41b so that it can be irradiated with substantially all of the primary light. The light conversion member 53 is arranged in such a manner that the central axis of the light conversion member 53 is arranged on the light axis 11. Further, the light conversion member 53 is arranged on the primary light incident portion 51 side to the secondary light emit portion 55 in the light axis 11 direction.

As shown in FIG. 1B, the light conversion member 53 has, e.g., a columnar shape. Therefore, light conversion member 53 has a circular rear surface 53a that faces the emit portion 41b and the primary light incident portion 51, a circular front surface 53b arranged on the front side to the rear surface 53a, and a curved peripheral surface 53c arranged between the rear surface 53a and the front surface 53b. It is to be noted that the light conversion member 53 may have, e.g., a discoid shape.

The rear surface 53a and the front surface 53b have the same size. The rear surface 53a and the front surface 53b are planes arranged to be orthogonal to the light axis 11. Central axes of the rear surface 53a and the front surface 53b are arranged on the light axis 11.

The rear surface 53a is arranged away from the emit portion 41b. In detail, the rear surface 53a is arranged away from the emit portion 41b and the primary light incident portion 51 so that a beam spot of the primary light formed on the rear surface 53a can be formed to be smaller than the rear surface 53a. The rear surface 53a functions as an irradiation surface that is irradiated with the primary light.

The peripheral surface 53c is arranged away from the radiation angle control member 59.

It is to be noted that a thickness of the light conversion member 53 and the concentration of the fluorescent particles or the diffusion particles are desirably set depending on how much of the primary light the light conversion member 53 converts into the secondary light.

[Secondary Light Emit Portion 55]

As shown in FIG. 1B, the secondary light emit portion 55 represents a front surface 57b of the light transmission member 57. The secondary light emit portion 55 has a circular shape.

[Light Transmission Member 57]

As shown in FIG. 1B, the light transmission member 57 has the rear surface 57a having the primary light incident portion 51 which is optically connected with the emit portion 41b and from which the primary light emitting from the emit portion 41b enters and the front surface 57b that functions as the secondary light emit portion 55 from which the secondary light emits. The rear surface 57a that includes the primary light incident portion 51 and the front surface 57b that functions as the secondary light emit portion 55 are planes arranged to be orthogonal to the light axis 11. Such a light transmission member 57 has, e.g., a truncated conical shape the diameter of which increases from the emit portion 41b toward the secondary light emit portion 55, i.e., from the rear side toward the front side in the light axis 11 direction. That is, the light transmission member 57 has, e.g., a truncated conical shape in which the rear surface 57a is formed to be smaller than the front surface 57b in the light axis 11 direction.

Furthermore, the light transmission member 57 contains the light conversion member 53, for example, in such a manner that the central axis of the light conversion member 53 and the central axis of the light transmission member 57 are arranged on the light axis 11, the light conversion member 53 is away from the emit portion 41b, the rear surface 57a, and the secondary light emit portion 55, and the beam spot of the primary light becomes smaller than the rear surface 53a of the light conversion member 53. That is, the light conversion member 53 is buried in the light transmission member 57.

In the light transmission member 57, the primary light and the secondary light are transmitted. Therefore, the light transmission member 57 is formed of a member through which the primary light emitting from the emit portion 41b and the secondary light emitting from the light conversion member 53 are transmitted. Such the member is formed of, e.g., an optically transparent member having high transmittance. This member has e.g., a silicone resin, glass, or quartz glass.

It is to be noted that the light transmission member 57 may be formed of a member that conducts heat outward when the light conversion member 53 generates the secondary light. Such the member has e.g., glass or a glass-based resin.

[Radiation Angle Control Member 59]

Such a radiation angle control member 59 as shown in FIG. 1B converts a traveling direction of the secondary light in such a manner that the secondary light emitting from the rear surface 53a and the peripheral surface 53c of the light conversion member 53 toward the radiation angle control member 59 in the secondary light emitting from the light conversion member 53 travels toward the adapter unit 800 through the secondary light emit portion 55. As a result, the radiation angle control member 59 controls a radiation angle of the secondary light. In detail, the radiation angle control member 59 functions as a reflection member that reflects the secondary light, which has emitted from the light conversion member 53 toward the radiation angle control member 59, toward the secondary light emit portion 55 that is the front side. The radiation angle control member 59 is arranged on an inner peripheral surface of the holding section 61.

In a region between the primary light incident portion 51 and the secondary light emit portion 55 arranged in the light axis 11 direction, the radiation angle control member 59 is arranged to surround this region. In detail, the radiation angle control member 59 is arranged on the entire peripheral surface 57c of the light transmission member 57 excluding the primary light incident portion 51 and the secondary light emit portion 55 to surround the light conversion member 53. Therefore, the radiation angle control member 59 is arranged away from the light conversion member 53 by the light transmission member 57.

The radiation angle control member 59 is formed by forming a film made of, e.g., a metal such as silver or aluminum. Alternatively, the radiation angle control member 59 may be formed by providing multiple layers of dielectric films. It is to be noted that the radiation angle control member 59 may be formed on the inner peripheral surface of the later-described holding section 61.

[Holding Section 61]

Such a holding section 61 as shown in FIG. 1B is made of, e.g., ceramics or stainless steel. The holding section 61 has, e.g., a columnar shape. The holding section 61 has a hollow portion 63 into which the light transmission member 57 including the radiation angle control member 59 is fitted. Therefore, for example, the hollow portion 63 has a truncated conical shape whose diameter increases from the rear side toward the front side in the light axis 11 direction. The hollow portion 63 has, e.g., a beam divergence angle larger than a beam divergence angle of the primary light. In the light axis 11 direction, the central axis of the hollow portion 63 coincides with the central axis of the holding section 61 and the light axis 11.

As shown in FIG. 1B, the hollow portion 63 penetrates through the holding section 61 in the light axis 11 direction. Therefore, the holding section 61 has an incident opening portion 63a arranged on a rear surface of the holding section 61 facing the emit portion 41b side and an emit opening portion 63b arranged on a front surface of the holding section 61. The incident opening portion 63a fits into the rear surface 57a of the light transmission member 57 so that the primary light can enter the primary light incident portion 51 from the emit portion 41b. The incident opening portion 63a is larger than the emit portion 41b and smaller than the emit opening portion 63b. The emit opening portion 63b is fitted into the secondary light emit portion 55 that is the front surface 57b of the light transmission member 57 so that the secondary light can emit.

Furthermore, the light transmission member 57 is fitted into the hollow portion 63 in such a manner that the central axis of the holding section 61 (the hollow portion 63) in the light axis 11 direction coincides with the central axis of the light transmission member 57 and the central axis of the light conversion member 53, the rear surface 57a of the light transmission member 57 is fitted into the incident opening portion 63a, and the secondary light emit portion 55 that is the front surface 57b of the light transmission member 57 is fitted into the emit opening portion 63b. In other words, the light transmission member 57 is filled in the hollow portion 63. At this time, the rear surface 57a of the light transmission member 57 and the rear surface of the holding section 61 are arranged on the same plane, and the front surface 57b of the light transmission member 57 and the front surface of the holding section 61 are arranged on the same plane.

As described above, to hold the primary light incident portion 51 and the secondary light emit portion 55, the holding section 61 has the incident opening portion 63a that is fitted into the primary light incident portion 51 side, the emit opening portion 63b that is fitted into the secondary light emit portion 55 side, and the hollow portion 63 that is continuous from the incident opening portion 63a side to the emit opening portion 63b side in the light axis 11 direction.

Moreover, in this case, as shown in FIG. 1B, the light conversion member 53 is arranged in the hollow portion 63 in such a manner that it is arranged away from the emit portion 41b and the primary light incident portion 51, arranged on the front side to the emit portion 41b and the primary light incident portion 51, arranged on the rear side to the secondary light emit portion 55, and covered with the radiation angle control member 59. In detail, the light transmission member 57 is fitted into the hollow portion 63, and the light conversion member 53 is contained in the light transmission member 57.

[Holding Section 70]

As shown in FIG. 1B, the holding section 70 has, e.g., a ferrule fixed to the holding section 61.

[Adapter Unit 800]

As shown in FIG. 1B and FIG. 10, the adapter unit 800 is attached to the illumination unit 50 in such a manner that the adapter unit 800 is arranged on the front side to the secondary light emit portion 55 and the central axis of the adapter unit 800 is arranged on the light axis 11. The adapter unit 800 according to this embodiment converts optical characteristics of the secondary light emitted from the optical illumination unit 400 and emits tertiary light different from the primary light and the secondary light as illumination light.

As shown in FIG. 1B, the adapter unit 800 has an adapter unit side incident portion 81 which is optically connected with the secondary light emit portion 55 and from which the secondary light emitting from the secondary light emit portion 55 enters. Additionally, as shown in FIG. 1B, the adapter unit 800 also has an adapter unit side light conversion member 83 that is arranged away from the adapter unit side incident portion 81, converts the optical characteristics of the secondary light when it is irradiated with the secondary light that has entered from the adapter unit side incident portion 81, and generates the tertiary light different from the secondary light as the illumination light. Further, as shown in FIG. 1B, the adapter unit 800 also has an adapter unit side emit portion 85 which is arranged on the front side to the adapter unit side light conversion member 83 and allows the tertiary light as the illumination light to emit outward therefrom.

Furthermore, as shown in FIG. 1B, the adapter unit 800 also has an adapter unit side light transmission member 87 that has the adapter unit side incident portion 81, is arranged between the adapter unit side incident portion 81 and the adapter unit side light conversion member 83 so that the secondary light can be transmitted there through, and arranged to be at least partially continuous from the adapter unit side incident portion 81 to the adapter unit side emit portion 85.

Moreover, as shown in FIG. 1B, the adapter unit 800 also has an adapter unit side reflection member 89 that is arranged on a peripheral surface 83c of the adapter unit side light conversion member 83 and a peripheral surface 87c of the adapter unit side light transmission member 87 and reflects the secondary light so that the secondary light can travel toward the adapter unit side emit portion 85. Additionally, as shown in FIG. 1B, the adapter unit 800 also has an adapter unit side holding section 91 that holds the adapter unit side light transmission member 87 including the adapter unit side incident portion 81, the adapter unit side light conversion member 83, the adapter unit side emit portion 85, and the adapter unit side reflection member 89.

These members included in the adapter unit 800 have concentric shapes having the light axis 11 as the central axis and are rotation-symmetrically arranged with the light axis 11 at the center.

[Adapter Unit Side Incident Portion 81]

The adapter unit side incident portion 81 represents a rear surface 87a of the adapter unit side light transmission member 87. This rear surface 87a represents, e.g., a plane arranged on the rearmost side of the adapter unit side light transmission member 87 in the light axis 11 side. The adapter unit side incident portion 81 has, e.g., a circular shape. The adapter unit side incident portion 81 is smaller than the adapter unit side emit portion 85.

[Size of Adapter Unit Side Incident Portion 81]

Figure 1D:
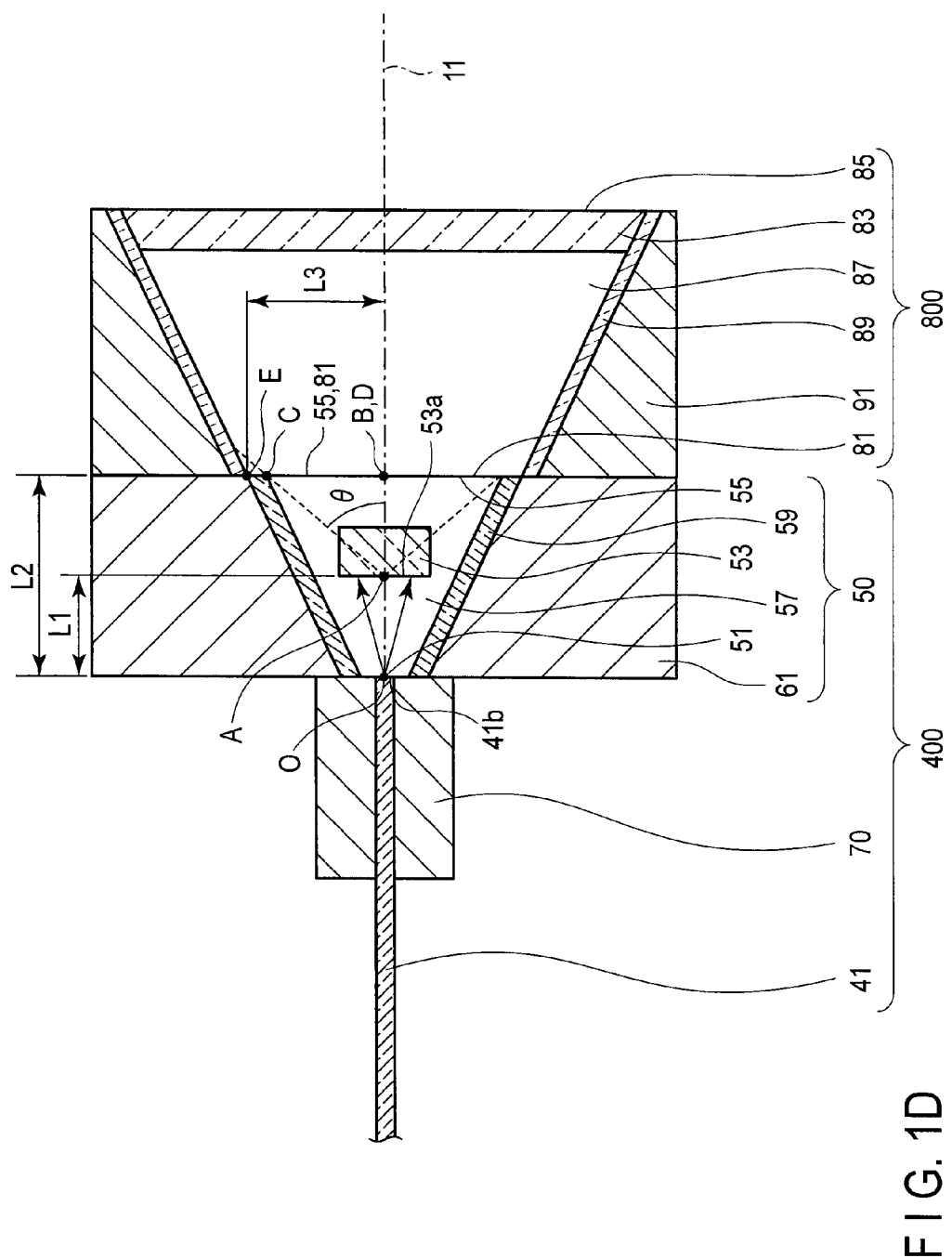
FIG. 1D is a view for explaining a radiation angle θ of secondary light.

A size of the adapter unit side incident portion 81 will now be described hereinafter with reference to FIG. 1D. It is to be noted that the size of the adapter unit side incident portion 81 is premised on a state that the adapter unit 800 is attached to the illumination unit 50.

The center of the emit portion 41b is determined as an origin O.

An intersection of the light axis 11 and the rear surface 53a of the light conversion member 53 is determined as a point A. The point A represents, e.g., the center of the rear surface 53a.

An intersection of the light axis 11 and the secondary light emit portion 55 is determined as a point B. The point B represents, e.g., the center of the secondary light emit portion 55.

In the secondary light emit portion 55, the farthest point from the point B is determined as a point C. The point C represents part of an edge of the secondary light emit portion 55.

An intersection of the light axis 11 and the adapter unit side incident portion 81 is determined as a point D. The point D represents, e.g., the center of the adapter unit side incident portion 81. It is to be noted that, since the adapter unit side incident portion 81 is connected to the secondary light emit portion 55, the point D overlaps the point B.

In the adapter unit side incident portion 81, the farthest point from the point D is determined as a point E. The point E represents part of an edge of the adapter unit side incident portion 81.

A distance between the origin O and the point A is determined as a distance L1.

A distance between the origin O and the point B is determined as a distance L2.

A distance between the point D and the point E is determined as a distance L3. The distance L3 represents a radius of the adapter unit side incident portion 81.

An angle formed between the points B, A, and C is determined as an angle θ. The angle θ represents the radiation angle of the secondary light.

At this time, $L3 \geq (L2-L1) \times \tan\theta$     Expression (1)

As described above, the adapter unit side incident portion 81 has the size that meets Expression (1), and it is substantially equal to the secondary light emit portion 55 in size or larger than the secondary light emit portion 55. Moreover, the adapter unit side incident portion 81 is smaller than the adapter unit side emit portion 85.

[Adapter Unit Side Light Conversion Member 83]

The adapter unit side light conversion member 83 is, e.g., a fluorescent substance that receives the secondary light, performs long wavelength conversion of the secondary light, and generates the tertiary light. As described above, the adapter unit side light conversion member 83 is a wavelength conversion member that converts a wavelength of the secondary light and also an optical member that functions when it is irradiated with the secondary light. It is to be noted that the adapter unit side light conversion member 83 may convert the light distribution of the secondary light.

As shown in FIG. 1B, the adapter unit side light conversion member 83 faces the adapter unit side incident portion 81 and is arranged ahead of the adapter unit side light transmission member 87 so that it can be irradiated with substantially all of the secondary light. Further, the adapter unit side light conversion member 83 is optically connected with a front surface 87b of the adapter unit side light transmission member 87 and arranged to cover an entire adapter unit side emit opening portion 93b of an adapter unit side hollow portion 93 arranged in the adapter unit side holding section 91. Furthermore, the adapter unit side light conversion member 83 is arranged so that the central axis of the adapter unit side light conversion member 83 is arranged on the light axis 11.

This adapter unit side light conversion member 83 has, e.g., a truncated conical shape whose diameter increases from the rear side toward the front side in the light axis 11 direction. The adapter unit side light conversion member 83 is a flat plate arranged to be orthogonal to the light axis 11.

The adapter unit side light conversion member 83 is formed by, e.g., adding an additive to a member through which the second light and the tertiary light are transmitted. This member has, e.g., a resin or glass, and the additive has, e.g., a cerium-activated YAG phosphor or a silicate-based fluorescent substance.

[Adapter Unit Side Emit Portion 85]

The Adapter unit side emit portion 85 represents the adapter unit side light conversion member 83.

[Adapter Unit Side Light Transmission Member 87]

The adapter unit side light transmission member 87 has the rear surface 87a that is optically connected with the secondary light emit portion 55 and functions as the adapter unit side incident portion 81 from which the secondary light emitting from the secondary light emit portion 55 enters, the front surface 87b that is optically connected with the adapter unit side light conversion member 83, and the peripheral surface 87c arranged between the rear surface 87a and the front surface 87b. The rear surface 87a and the front surface 87b are planes arranged to be orthogonal to the light axis 11. Such an adapter unit side light transmission member 87 has, e.g., a truncated conical shape whose diameter increases from the rear surface 87a toward the front surface 87b in the light axis 11 direction. The peripheral surface 87c is smoothly continuous with the peripheral surface 83c of the adapter unit side light conversion member 83.

The secondary light is transmitted through the adapter unit side light transmission member 87. The adapter unit side light transmission member 87 is formed of a member through which the secondary light is transmitted. Such a member is formed of, e.g., an optically transparent member having high transmittance. This member has, e.g., a silicone resin, glass, or quartz glass.

It is to be noted that the adapter unit side light transmission member 87 may be formed of a member that conducts heat, which is produced when the adapter unit side light conversion member 83 generates the secondary light, to the outside. Such a member has, e.g., glass or a glass-based resin.

[Adapter Unit Side Reflection Member 89]

In a region between the adapter unit side incident portion 81 and the adapter unit side emit portion 85 arranged in the light axis 11 direction, the adapter unit side reflection member 89 is arranged to surround this region. In detail, the adapter unit side reflection member 89 is arranged on the entire peripheral surface 83c of the adapter unit side light conversion member 83 excluding the adapter unit side emit portion 85 and the entire peripheral surface 87c of the adapter unit side light transmission member 87 excluding the rear surface 87a and the front surface 87b to surround the adapter unit side light conversion member 83 and the adapter unit side light transmission member 87. It is to be noted that the adapter unit side reflection member 89 may be arranged on the inner peripheral surface of the adapter unit side holding section 91.

[Adapter Unit Side Holding Section 91]

The adapter unit side holding section 91 is made of, e.g., ceramics or stainless steel. The adapter unit side holding section 91 has, e.g., a columnar shape. The adapter unit side holding section 91 is mechanically connected to the holding section 61 so that the adapter unit side incident portion 81 can be optically connected to the secondary light emit portion 55. The adapter unit side holding section 91 has the adapter unit side hollow portion 93 in which the adapter unit side light conversion member 83 and the adapter unit side light transmission member 87 including the adapter unit side reflection member 89 are fitted. Therefore, for example, the adapter unit side hollow portion 93 has a truncated conical shape whose diameter increases from the rear side toward the front side in the light axis 11 direction. The adapter unit side hollow portion 93 has a beam divergence angle that is substantially equal to a beam divergence angle of the hollow portion 63 or larger than the beam divergence angle of the hollow portion 63. In the light axis 11 direction, the central axis of the adapter unit side hollow portion 93 coincides with the central axis of the adapter unit side holding section 91 and the light axis 11.

The adapter unit side hollow portion 93 penetrates through the adapter unit side holding section 91 in the light axis 11 direction. Therefore, the adapter unit side holding section 91 has an adapter unit side incident opening portion 93a that is arranged on the rear surface of the adapter unit side holding section 91 facing the holding section 61 side and an adapter unit side emit opening portion 93b arranged on the front surface of the adapter unit side holding section 91. The adapter unit side incident opening portion 93a is substantially equal to the emit opening portion 63b or larger than the emit opening portion 63b, and smaller than the adapter unit side emit opening portion 93b. The adapter unit side incident opening portion 93a is fitted to the adapter unit side incident portion 81 that is the rear surface 87a of the adapter unit side light transmission member 87 so that the secondary light can enter from the secondary light emit portion 55. The adapter unit side emit opening portion 93b is fitted to the adapter unit side light conversion member 83.

Moreover, the adapter unit side light conversion member 83 and the adapter unit side light transmission member 87 are fitted into the adapter unit side hollow portion 93 in such a manner that the central axis of the adapter unit side holding section 91 (the adapter unit side hollow portion 93) in the light axis 11 direction coincides with the central axis of the adapter unit side light conversion member 83 and the central axis of the adapter unit side light transmission member 87. Additionally, the adapter unit side light transmission member 87 and the adapter unit side light conversion member 83 are fitted in the adapter unit side hollow portion 93 in such a manner that the adapter unit side incident portion 81 is fitted into the adapter unit side incident opening portion 93a and the adapter unit side light conversion member 83 is fitted into the adapter unit side emit opening portion 93b. At this time, the adapter unit side light conversion member 83 and the front surface of the adapter unit side holding section 91 are arranged on the same plane, and the rear surface 87a of the adapter unit side light transmission member 87 and the rear surface of the adapter unit side holding section 91 are arranged on the same plane.

As described above, to hold the adapter unit side incident portion 81 and the adapter unit side emit portion 85, the adapter unit side holding section 91 has the adapter unit side incident opening portion 93a fitted into the adapter unit side incident portion 81 side, the adapter unit side emit opening portion 93b fitted into the adapter unit side emit portion 85 side, and the adapter unit side hollow portion 93 that is continuous from the adapter unit side incident opening portion 93a side to the adapter unit side emit opening portion 93b side in the light axis 11 direction.

Further, in this case, as shown in FIG. 1B, the adapter unit side light conversion member 83 is arranged in the adapter unit side hollow portion 93.

[Operation]

As shown in FIG. 1A and FIG. 1B, the adapter unit 800 is attached to the illumination unit 50 in such a manner that the adapter unit side incident portion 81 is optically connected to the secondary light emit portion 55 and the central axis of the adapter unit 800 is arranged on the light axis 11.

The primary light travels in the light transmission member 57 with the beam divergence angle θ corresponding to the numerical aperture Fna of the light guide member 41 and a refractive index n of the light transmission member 57.

In this case, the beam divergence angle θ is represented by the following expression.

$$n \times \sin \theta = Fna \qquad \text{Expression (2)}$$

When Expression (2) is converted, the following expression can be provided.

$$\theta = \sin^{-1}(Fna/n) \qquad \text{Expression (3)}$$

The light conversion member 53 is irradiated with the primary light, and the light conversion member 53 generates the secondary light based on the primary light. The secondary light is diffused by the light conversion member 53 and allowed to emit from the light conversion member 53 toward the light transmission member 57. At this time, the secondary light is allowed to emit in various directions, e.g., a frontward direction, a rearward direction, and a lateral direction. Therefore, part of the secondary light directly travels to the adapter unit 800, and the other part of the secondary light is applied to the radiation angle control member 59.

In the secondary light that is applied to the radiation angle control member 59, a traveling direction of the secondary light is converted by the radiation angle control member 59 so that the secondary light travels toward the adapter unit 800 through the secondary light emit portion 55. In detail, the radiation angle control member 59 reflects the secondary light so that the secondary light travels toward the adapter unit 800 via the secondary light emit portion 55.

It is to be noted that, in this embodiment, the light conversion member 53 is arranged on the primary light incident portion 51 side of the secondary light emit portion 55. However, the light transmission member 57 has the truncated conical shape whose diameter increases toward the front side, the radiation angle control member 59 is arranged, and the secondary light emit portion 55 is larger than the primary light incident portion 51. Therefore, in part of the secondary light that directly travels toward the adapter unit 800 and the other part of the secondary light whose traveling direction has been converted by the radiation angle control member 59, the secondary light travels toward the adapter unit 800 without being blocked by the secondary light emit portion 55.

Further, the adapter unit side incident portion 81 is substantially equal to the secondary light emit portion 55 in size, or it is larger than the secondary light emit portion 55. Therefore, the secondary light efficiently travels to the adapter unit 800 without leaking.

Furthermore, the secondary light enters the adapter unit 800 from the adapter unit side incident portion 81, and it is transmitted through the adapter unit side light transmission member 87. Moreover, part of the secondary light is directly applied to the adapter unit side light conversion member 83, and the other part of the secondary light is reflected by the adapter unit side reflection member 89 and applied to the adapter unit side light conversion member 83.

Additionally, the adapter unit side light conversion member 83 generates the tertiary light based on the secondary light. The tertiary light is allowed to emit from the adapter unit side emit portion 85 and illuminates an illumination target as illumination light.

It is to be noted that, in the secondary light reflected by the adapter unit side reflection member 89 and the tertiary light, part of the secondary and tertiary light is returned to the illumination unit 50. Further, a traveling direction of the part of the secondary and tertiary light is converted by the radiation angle control member 59, and such light re-enters the adapter unit 800 from the adapter unit side incident portion 81.

It is to be noted that, as shown in FIG. 10, when the adapter unit 800 has been detached from the illumination unit 50, the secondary light is allowed to emit from the secondary light emit portion 55 and illuminates the illumination target as the illumination light. At this time, the secondary light functions as diffused light by the light conversion member 53.

[Effect]

As described above, in this embodiment, the radiation angle control member 59 is arranged in the illumination unit 50, and the radiation angle control member 59 controls the radiation angle of the secondary light. As a result, in this embodiment, the secondary light can be efficiently guided to the adapter unit 800. Further, in this embodiment, even if the secondary light and the tertiary light are returned from the adapter unit 800 to the illumination unit 500, the secondary light and the tertiary light can be efficiently returned to the adapter unit 800 by the radiation angle control member 59, and the secondary light and the tertiary light can be efficiently guided to the adapter unit 800. As described above, in this embodiment, the light can be efficiently guided to the adapter unit 800 from the optical illumination unit 400. Furthermore, in this embodiment, the utilization efficiency of the light can be improved.

Furthermore, in this embodiment, the light transmission member 57 has the truncated conical shape whose diameter increases toward the front side, and the secondary light emit portion 55 is larger than the primary light incident portion 51 in size. Therefore, in this embodiment, the secondary light can be guided to the adapter unit 800 without being blocked by the secondary light emit portion 55.

Moreover, in this embodiment, the light transmission member 57 has, e.g., the truncated conical shape whose diameter increases from the primary light incident portion 51 toward the secondary light emit portion 55 in the light axis 11 direction, and the radiation angle control member 59 is arranged on the peripheral surface 53c of the light conversion member 53. Therefore, in this embodiment, the secondary light can be assuredly guided to the adapter unit 800 by the radiation angle control member 59.

Additionally, in this embodiment, the light conversion member 53 is arranged away from the emit portion 41b so that a beam spot of the primary light can be formed smaller than the rear surface 53a of the light conversion member 53. Therefore, in this embodiment, the light conversion member 53 can be assuredly irradiated with the primary light, and the secondary light can be assuredly generated.

Further, in this embodiment, the light conversion member 53 is contained in the light transmission member 57. Therefore, in this embodiment, the light conversion member 53 can be prevented from coming off the light transmission member 57. Furthermore, in this embodiment, when the light conversion member 53 allows the secondary light to emit therefrom, the light conversion member 53 generates heat. At this time, the light conversion member 53 can efficiently conduct the heat to the light transmission member 57.

Moreover, in this embodiment, the adapter unit side incident portion 81 is substantially equal to the secondary light emit portion 55 in size, or it is larger than the secondary light emit portion 55. Therefore, in this embodiment, the secondary light can be efficiently guided to the adapter unit 800 without leaking. Additionally, even if the secondary light and the tertiary light are returned from the adapter unit 800 to the illumination unit 50, the secondary light and the tertiary light can be efficiently guided to the adapter unit 800 without leaking, as described above.

Further, in this embodiment, the adapter unit side light transmission member 87 has the truncated conical shape whose diameter increases toward the front side, and the adapter unit side emit portion 85 is larger than the adapter unit side incident portion 81 in size. Therefore, in this embodiment, the secondary light can be guided to the adapter unit side light conversion member 83 without being blocked by the adapter unit side emit portion 85.

Furthermore, in this embodiment, the adapter unit side light transmission member 87 has, e.g., the truncated conical shape whose diameter increases toward the front side, and the adapter unit side light conversion member 83 is arranged ahead of the adapter unit side light transmission member 87. Moreover, the adapter unit side reflection member 89 is arranged on the peripheral surface 83c of the adapter unit side light conversion member 83 and the peripheral surface 87c of the adapter unit side light transmission member 87. Therefore, the secondary light can be assuredly guided to the adapter unit side light conversion member 83 by the adapter unit side reflection member 89.

Additionally, in this embodiment, when the adapter unit 800 has been detached from the illumination unit 50, the illumination target is illuminated with the secondary light as the illumination light. At this time, the secondary light functions as the diffused light by the light conversion member 53. As described above, in this embodiment, since an emit angle (a radiation field) of the secondary light can be enlarged and the secondary light can be allowed to emit, the secondary light can be diffused, and the density of the secondary light immediately after emitting from the secondary light emit portion 55 can be reduced. Further, as a result, in this embodiment, it is possible to avoid a burden imposed on a user due to the secondary light, and desired safety can be maintained.

It is to be noted that the light conversion member 53 includes the fluorescent substance or the like in this embodiment, but the present invention is not restricted thereto.

A: For example, the light conversion member 53 may have at least one of a concave lens, a convex lens, a hologram lens, and a diffraction grating. The concave lens, the convex lens, and a combination of the concave lens and the convex lens function as the radiation angle conversion member that converts the radiation angle of the secondary light. The hologram lens and the diffraction grating function as the radiation angle conversion member or a light distribution conversion member that converts a radiating direction of the secondary light.

B: For example, the light conversion member 53 may be made of a resin having particles dispersed therein or glass. These particles may be formed of, e.g., alumina with a high refractive index and a high reflection factor. Alternatively, for example, the light conversion member 53 may be formed by mixing optically transparent members having different refractive indexes each other. Alternatively, for example, the light conversion member 53 may be formed of a scattering plate of obscured glass or the like or a diffusion plate having minute irregularities arranged on a surface thereof.

C: For example, the light conversion member 53 may be formed of a spectral conversion member having at least one of an optical semiconductor material, an SHG (second-order harmonic generation) material, and a photoluminescence material.

D, E: For example, the light conversion member 53 may be formed of a member that allows part of the primary light to be transmitted there through and blocks the other part of the primary light.

D: This member is, e.g., an optical filter. This optical filter has at least one of, e.g., a wavelength cut filter, a dye filter, and an optical resonator (an etalon).

E: This member is, e.g., a light transmitting modulation member. The light transmitting modulation member has at least one of, e.g., a light switch, electrochromic, and a liquid crystal device.

For example, B or D is suitable for safety of the light source section 21 or reduction of laser. Further, when the light source section 21 emits the primary light representing at least one of lamp light and LED light and a radiation angle of this primary light is adjusted, at least one of A and B can be used.

The light conversion member 53 is not restricted to the above, and it may be constituted of a combination of these members. It is to be noted that the light conversion member 53 has been described, but this point can be also applied to the adapter unit side light conversion member 83.

Further, in this embodiment, optically connecting the light source section 21 to the light guide member 41 can suffice. Such a light source section 21 has, e.g., one of a xenon lamp, a metal halide lamp, an LED, a gas laser, a solid-state laser, and others.

Furthermore, in this embodiment, the light guide member 41 is not restricted to a single optical fiber strand. The light guide member 41 may be formed of a bundle fiber. The light guide member 41 may have a light pipe. Moreover, the light guide member 41 may be formed of a light wave guide having a first light path that has a high refractive index and a second light path that has a low refractive index and surrounds the first light path. Such a light wave guide has, e.g., a slab type light wave guide device or a flexible light wave guide device. As described above, the light guide member 41 may be formed of at least one of a single optical fiber strand, a bundle fiber, a light pipe, and a light wave guide device.

Additionally, the light source apparatus 10 according to this embodiment can be used as, e.g., a light source apparatus for an industrial or medical endoscope.

[First Modification]

[Configuration]

A configuration and others different from the first embodiment will now be described hereinafter with reference to FIG. 2A.

[Light Conversion Member 53]

Figure 2A:
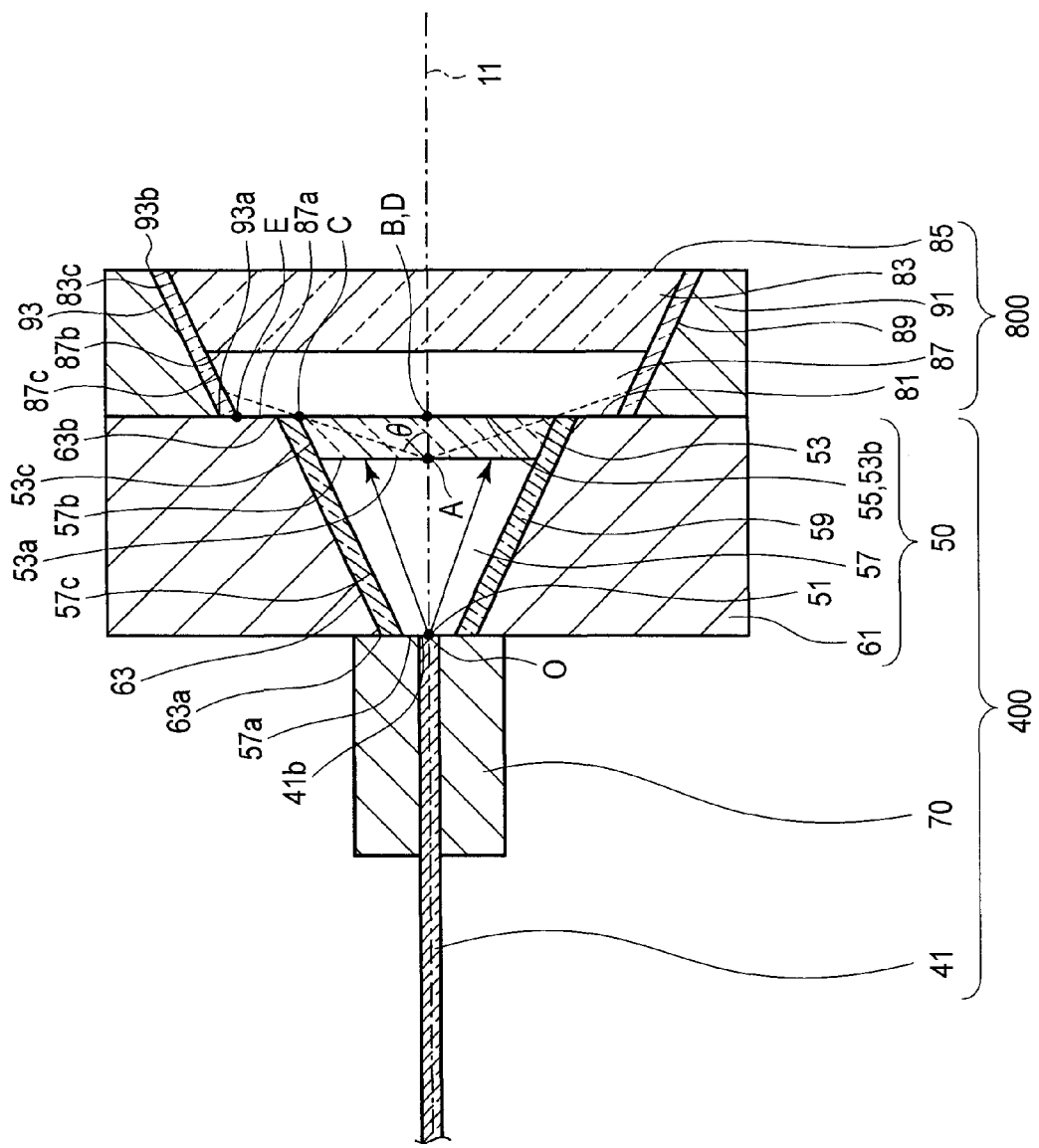
FIG. 2A is a view showing an optical configuration of an optical illumination unit and an adapter unit according to a first modification of the first embodiment.

As shown in FIG. 2A, the light conversion member 53 according to this modification is arranged ahead of the light transmission member 57 and has the secondary light emit portion 55. In detail, the light conversion member 53 has the rear surface 53a that is optically connected to the front surface 57b of the light transmission member 57 and the front surface 53b that functions as the secondary light emit portion 55. Therefore, the light conversion member 53 is not contained in the light transmission member 57, and is arranged outside the light transmission member 57 so that it is optically connected to the front surface 57b of the light transmission member 57. Further, the light transmission member 57 is arranged to cover the entire surface of the emit opening portion 63b of the holding section 61.

In this case, the light conversion member 53 has, e.g., the truncated conical shape whose diameter increases from the rear side toward the front side in the light axis 11 direction. Furthermore, the peripheral surface 53c of the light conversion member 53 is smoothly continuous with the peripheral surface 57c of the light transmission member 57.

[Light Transmission Member 57]

As shown in FIG. 2A, the light transmission member 57 has the primary light incident portion 51. Moreover, the light transmission member 57 is arranged between the primary light incident portion 51 and the light conversion member 53, and is arranged to be at least partially continuous from the primary light incident portion 51 to the light conversion member 53 so that the primary light and the secondary light can be transmitted there through.

[Radiation Angle Control Member 59]

The radiation angle control member 59 is arranged on the entire peripheral surface 53c of the light conversion member 53 and the entire peripheral surface 57c of the light transmission member 57 excluding the primary light incident portion 51 and the secondary light emit portion 55. In this state, the light conversion member 53 and the light transmission member 57 are fitted into the hollow portion 63.

Additionally, the radiation angle control member 59 controls a radiation angle of the secondary light so that the secondary light emitting from the secondary light emit portion 55 travels toward a wide region including a plane orthogonal to the light axis 11.

[Adapter Unit Side Incident Portion 81]

As described above, the light conversion member 53 is arranged in the secondary light emit portion 55, and the radiation angle control member 59 controls the radiation angle of the secondary light. Therefore, in the secondary light emitting from the secondary light emit portion 55 toward, e.g., the adapter unit 800, the radiation angle θ of the secondary light according to this modification is larger than the radiation angle θ of the secondary light according to the first embodiment.

Therefore, the adapter unit side incident portion 81 is formed to be larger than the secondary light emit portion 55 so that the secondary light emitting from the secondary light emit portion 55 can enter the adapter unit 800 from the adapter unit side incident portion 81 without leaking. Specifically, a linear extended line connecting the point A with the point C abuts on the adapter unit side reflection member 89. Such an adapter unit side incident portion 81 is, e.g., 1.2 times as large as the secondary light emit portion 55.

[Effect]

In this modification, since the light conversion member 53 does not have to be contained in the light transmission member 57, the light conversion member 53 can be easily arranged in the holding section 61. Furthermore, in this modification, since the light conversion member 53 is arranged in the entire secondary light emit portion 55, the light conversion member 53 can be assuredly irradiated with the primary light. Moreover, in this modification, the light conversion member 53 is arranged to cover the entire surface of the emit opening portion 63b of the holding section 61, and the light conversion member 53 is assuredly irradiated with the primary light. Therefore, the need for precise relative positioning of the emit portion 41b and the light conversion member 53 can be eliminated.

Additionally, in this modification, the light conversion member 53 can increase the radiation angle θ of the secondary light to be larger than the radiation angle θ of the secondary light according to the first embodiment. Therefore, in this modification, when the adapter unit 800 has been detached from the illumination unit 50, the secondary light can be further diffused, and the density of the secondary light immediately after emitting from the secondary light emit portion can be further reduced. Furthermore, as a result, in this modification, it is possible to prevent a burden from being imposed on a user due to the secondary light, and desired safety can be further maintained.

Moreover, in this modification, the adapter unit side incident portion 81 is formed to be larger than the secondary light emit portion 55. Therefore, in this modification, even if the radiation angle θ of the secondary light is larger than the radiation angle θ of the secondary light according to the first embodiment, the secondary light can be guided to the adapter unit 800 from the optical illumination unit 400 without leaking.

[Second Modification]
[Configuration]

Figure 2B:
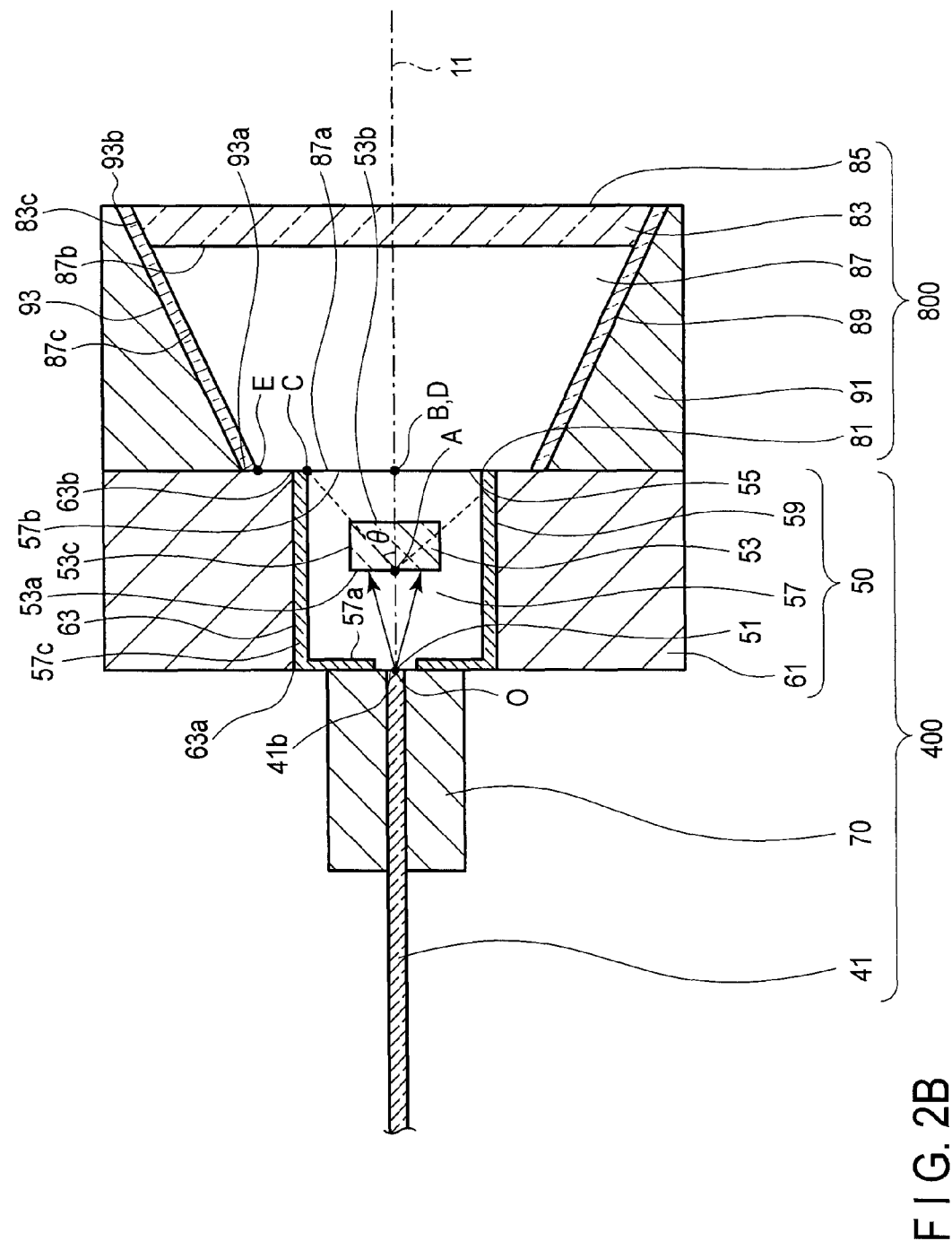
FIG. 2B is a view showing an optical configuration of an optical illumination unit and an adapter unit according to a second modification of the first embodiment.

A configuration and others different from the first embodiment will now be described hereinafter with reference to FIG. 2B.

[Light Transmission Member 57]

The light transmission member 57 has, e.g., a columnar shape. In this case, the rear surface 57a and the front surface 57b are flat surfaces arranged to be orthogonal to the light axis 11, and they have the same size.

[Radiation Angle Control Member 59]

The radiation angle control member 59 is arranged on the rear surface 57a of the light transmission member 57 excluding the primary light incident portion 51 and the entire peripheral surface 57c of the light transmission member 57.

[Hollow Portion 63]

The hollow portion 63 has a columnar shape to correspond to the light transmission member 57. The light transmission member 57 including the radiation angle control member 59 is fitted into the hollow portion 63.

[Adapter Unit Side Incident Portion 81]

It has the same configuration as that in the first modification.

[Effect]

Although each of the hollow portion 63 and the light transmission member 57 has the truncated conical shape in the first embodiment, each of the hollow portion 63 and the light transmission member 57 has a columnar shape in this modification. Therefore, in this modification, the hollow portion 63 and the light transmission member 57 can be easily processed as compared with the first embodiment.

[Third Modification]
[Configuration]

Figure 2C:
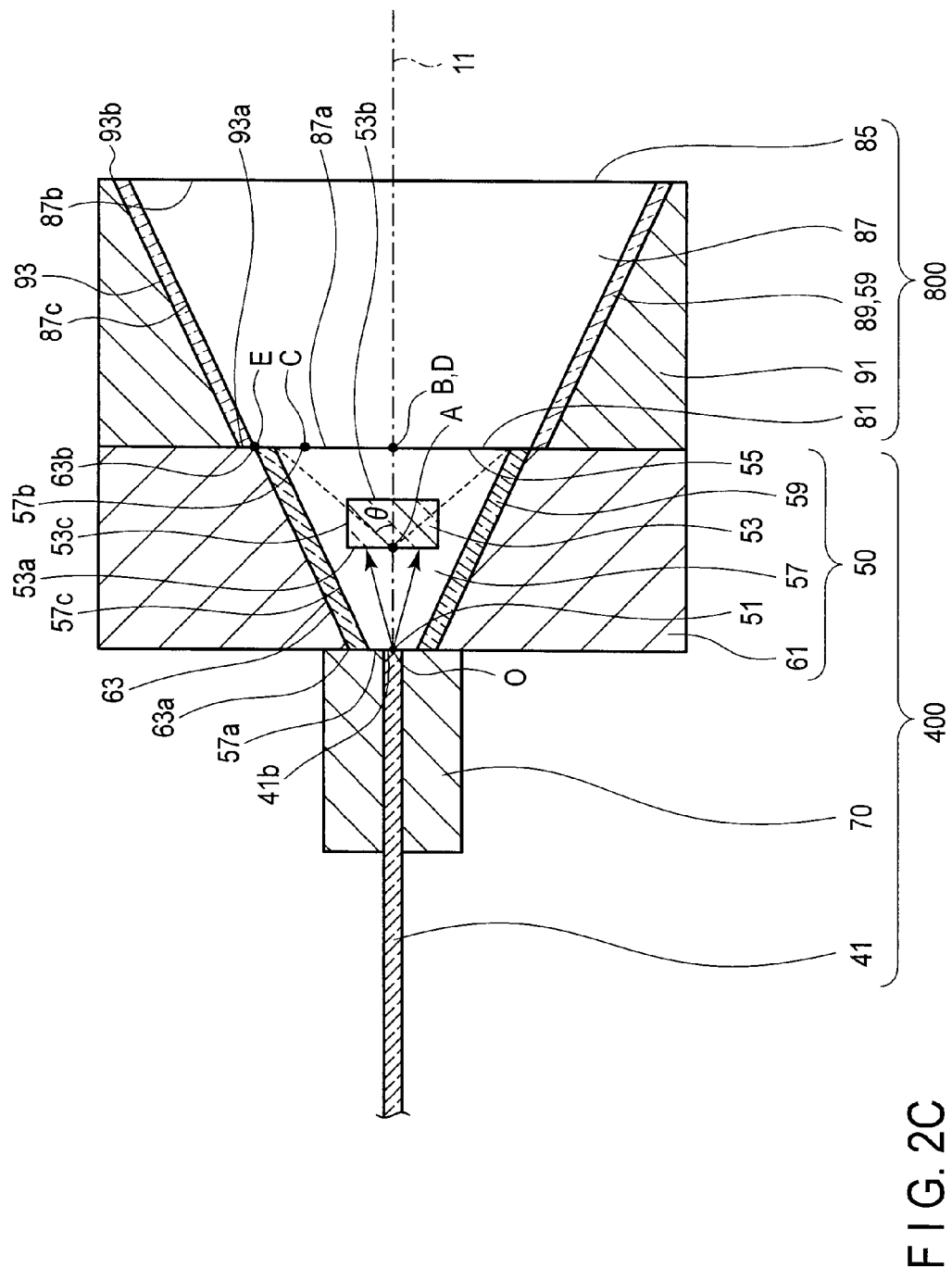
FIG. 2C is a view showing an optical configuration of an optical illumination unit and an adapter unit according to a third modification of the first embodiment.

A configuration and others different from the first embodiment will now be described hereinafter with reference to FIG. 2C.

[Adapter Unit 800]

The adapter unit 800 emits the secondary light alone as illumination light.

[Adapter Unit Side Light Conversion Member 83]

Since the adapter unit 800 emits the secondary light alone as the illumination light, the adapter unit side light conversion member 83 is omitted.

[Adapter Unit Side Reflection Member 89]

The adapter unit side reflection member 89 functions as the radiation angle control member 59.

[Effect]

In this modification, the radiation angle of the secondary light can be efficiently controlled by the adapter unit side reflection member 89. Additionally, in this modification, the configuration of the adapter unit 800 can be simplified.

[Fourth Modification]
[Configuration]

A configuration and others different from the first embodiment will now be described hereinafter.

[Light Conversion Member 53/Adapter Unit Side Light Conversion Member 83]

The light conversion member 53 is formed of at least one of the diffusion member, the spectral conversion member, the light distribution conversion member, the wavelength selection filter, a dimming member, and the optical member.

The adapter unit side light conversion member 83 is formed of at least one of the spectral conversion member, the light distribution conversion member, the wavelength selection filter, the dimming member, and the optical member.

The diffusion member increases a radiation angle of light and diffuses the light, for example.

The spectral conversion member allows light having a different spectral shape to emit therefrom.

The light distribution conversion member converts a light distribution characteristic of light without converting a spectral shape of the light.

The wavelength selection filter selects a spectrum in a desired wavelength domain from a spectral shape of light and allows the spectrum to be transmitted there through.

The dimming member dims light without changing a spectral shape of the light.

The optical lens converts a radiation angle of light.

[Effect]

In this modification, for example, it is assumed that the light conversion member 53 is made of a fluorescent substance and the adapter unit side light conversion member 83 is formed of the diffusion member. In this case, even if the adapter unit 800 is detached from the optical illumination unit 400 and the optical illumination unit 400 alone is used, the secondary light can be used as illumination light. Furthermore, in this case, when the adapter unit 800 is attached to the optical illumination unit 400, the adapter unit 800 can diffuse and emit the illumination light. As a result, an illumination target can be evenly irradiated with the illumination light.

As described above, in this modification, a degree of freedom in design of the light source apparatus 10 can be improved.

Second Embodiment

[Configuration]

Figure 3:
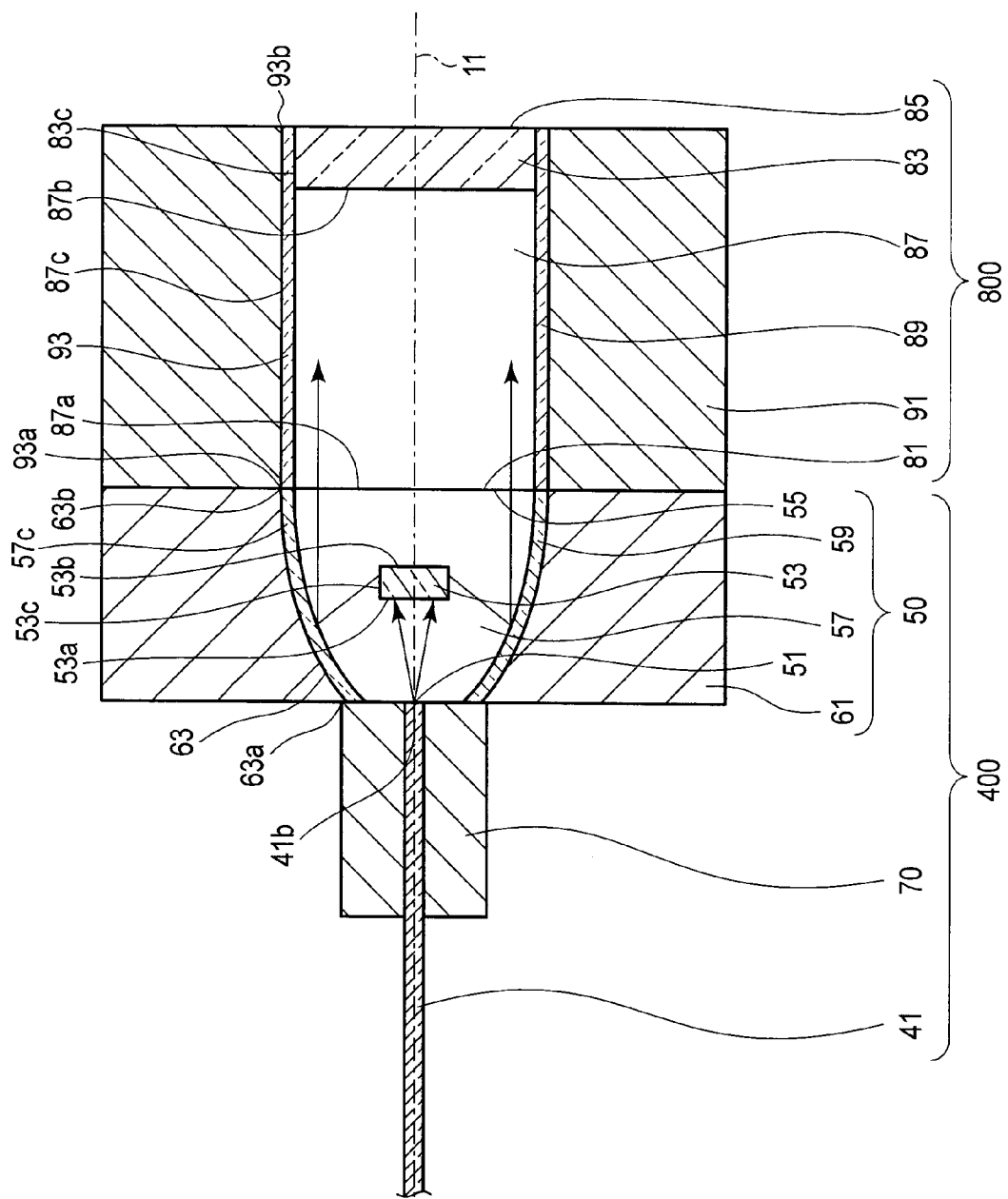
FIG. 3 is a view showing an optical configuration of an optical illumination unit and an adapter unit according to a second embodiment.

In this embodiment, a configuration different from the configuration of the first embodiment alone will be described hereinafter with reference to FIG. 3.

[Light Transmission Member 57]

A light transmission member 57 has a parabolic shape. In this case, like the first embodiment, a secondary light emit portion 55 is larger than a primary light incident portion 51 in size. The light transmission member 57 is arranged in such a manner that an axis of a parabola is arranged on a light axis 11.

[Light Conversion Member 53]

A light conversion member 53 is arranged in such a manner that a central axis of the light conversion member 53 is arranged on the light axis 11 and the light conversion member 53 includes a focal point of the parabola. In detail, it is satisfactory to arrange a region between the center of the light conversion member 53 and a rear surface 53a of the light conversion member 53 as an incident surface in the vicinity of the focal point of the parabola.

[Radiation Angle Control Member 59]

A radiation angle control member 59 is arranged on an entire parabola shape peripheral surface 57c of the parabolic light transmission member 57 excluding the primary light incident portion 51 and the secondary light emit portion 55. In this state, the light transmission member 57 is fitted into a hollow portion 63.

The radiation angle control member 59 converts a traveling direction of secondary light emitting from the light conversion member 53 to a rear side of the light conversion member 53 and a lateral side of the light conversion member 53 in such a manner that the secondary light can be made nearly parallel light that is nearly parallel to the light axis 11 and travels to the secondary light emit portion 55.

[Hollow Portion 63]

The hollow portion 63 has a parabolic shape to correspond to the light transmission member 57. In this case, like the first embodiment, an incident opening portion 63a is larger than an emit opening portion 63b in size. The light transmission member 57 including the radiation angle control member 59 is fitted into the hollow portion 63.

[Adapter Unit 800]

[Adapter Unit Side Incident Portion 81/Adapter Unit Side Light Transmission Member 87]

An adapter unit side light transmission member 87 has a columnar shape having a diameter substantially equal to a maximum diameter of the light transmission member 57 or a diameter larger than the maximum diameter. Therefore, an adapter unit side incident portion 81 that is a rear surface 87a of the adapter unit side light transmission member 87 and a front surface 87b of the adapter unit side light transmission member 87 have a size substantially equal to the secondary light emit portion 55 or a size larger than the secondary light emit portion 55. The adapter unit side incident portion 81 and the front surface 87b of the adapter unit side light transmission member 87 are flat surfaces that have the same size and are arranged to be orthogonal to the light axis 11.

[Adapter Unit Side Emit Portion 85/Adapter Unit Side Light Conversion Member 83]

An adapter unit side light conversion member 83 (an adapter unit side emit portion 85) has a columnar shape having a diameter substantially the same as the adapter unit side light transmission member 87 (the adapter unit side incident portion 81). The adapter unit side light conversion member 83 is a flat surface arranged to be orthogonal to the light axis 11. A peripheral surface 83c of the adapter unit side light conversion member 83 is smoothly continuous with a peripheral surface 87c of the adapter unit side light transmission member 87.

[Adapter Unit Side Hollow Portion 93]

An adapter unit side hollow portion 93 has a columnar shape to correspond to the adapter unit side light conversion member 83 and the adapter unit side light transmission member 87. The adapter unit side light conversion member 83 and the adapter unit side light transmission member 87 including the adapter unit side reflection member 89 are fitted into the adapter unit side hollow portion 93.

[Operation]

The light conversion member 53 is arranged to include a focal point of a parabola. Therefore, in the secondary light that has emitted to the rear side to the light conversion member 53 and the lateral side of the light conversion member 53, the secondary light travels toward the parabolic radiation angle control member 59.

Further, a traveling direction of the secondary light is converted by the radiation angle control member 59. As a result, the secondary light travels toward the secondary light emit portion 55 as the nearly parallel light that is nearly parallel to the light axis 11. The secondary light enters the adapter unit 800 from the adapter unit side incident portion 81 as the parallel light and is applied to the adapter unit side light conversion member 83. The adapter unit side light conversion member 83 generates tertiary light based on the secondary light. The tertiary light is allowed to emit from the adapter unit side emit portion 85, and an illumination target is illuminated with it as illumination light.

[Effect]

In this embodiment, each of the light transmission member 57 and the radiation angle control member 59 has the parabolic shape, and the light conversion member 53 is arranged to include the focal point of the parabola. As a result, in this embodiment, even if the secondary light is allowed to emit to the rear side to the light conversion member 53 and the lateral side of the light conversion member 53, the secondary light can be converted into the parallel light by the radiation angle control member 59. Therefore, in this embodiment, the secondary light can be efficiently guided to the adapter unit 800.

Furthermore, in this embodiment, since the secondary light is the parallel light, a size of an illumination unit 50 and a size of the adapter unit 800 can be reduced.

It is to be noted that this embodiment can be combined with at least one of the respective modifications of the first embodiment.

Third Embodiment

[Configuration]

Figure 4:
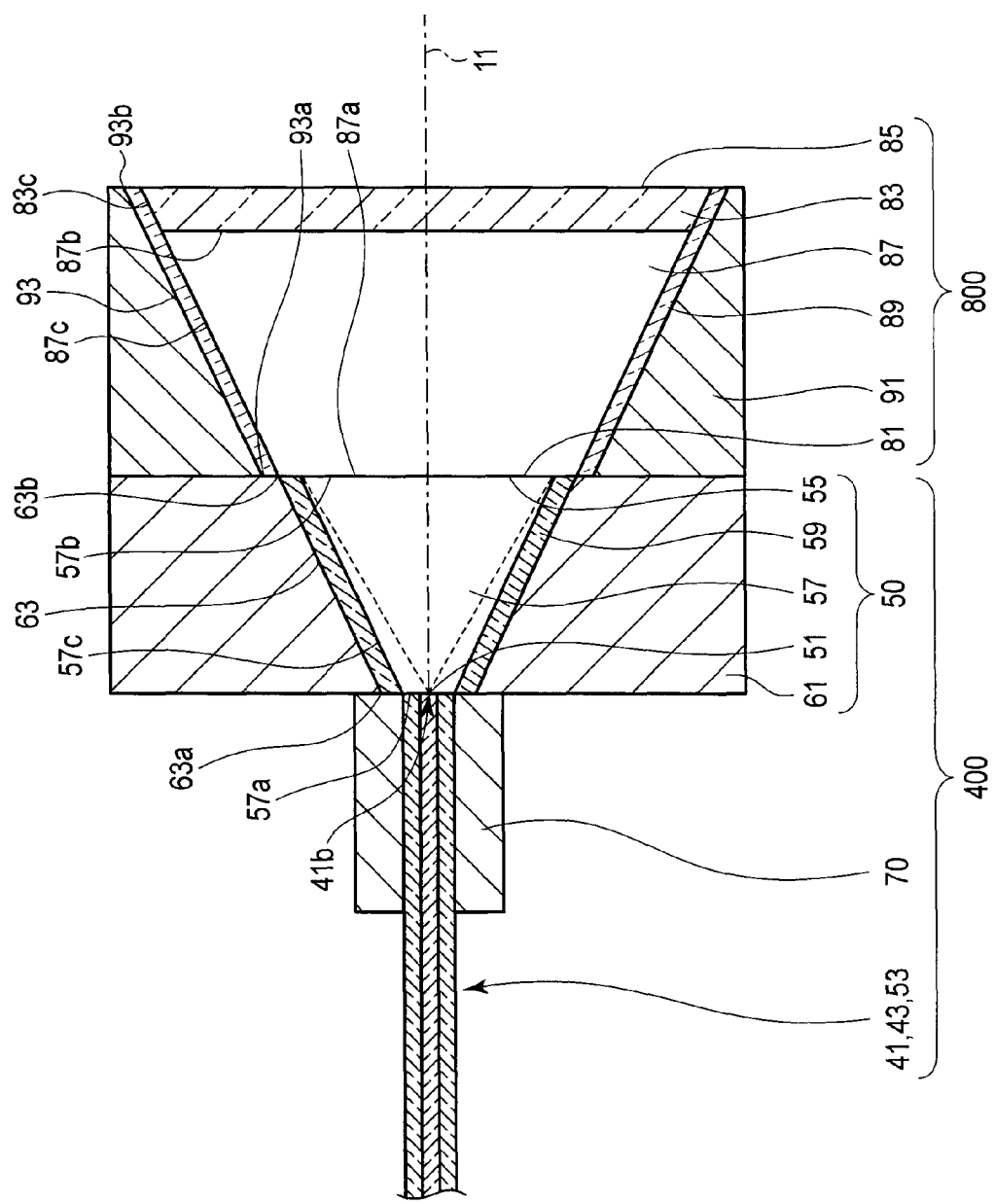
FIG. 4 is a view showing an optical configuration of an optical illumination unit and an adapter unit according to a third embodiment.

In this embodiment, a configuration different from the configuration in the first embodiment alone will be described hereinafter with reference to FIG. 4.

[Light Guide Member 41]

A light guide member 41 has a bundle fiber 43 formed by bundling optical fiber strands. Such a light guide member 41 is, e.g., a light guide. The number of the optical fibers is, e.g., several hundred to several thousand. The optical fibers have the same numerical aperture Fna.

In this case, a central axis of the light guide member 41 represents a central axis of an effective optical light guide region formed by bundling the optical fiber strands.

The optical fibers have, e.g., softness and flexibility and are bendable. In the light guide member 41 formed of the optical fibers, a light path length of each optical fiber and a shape of each optical fiber vary in accordance with bending of the light guide member 41. As a result, optical characteristics of primary light are converted before the primary light that has entered from an incident portion 41a is guided to an emit portion 41b, secondary light is generated, and the secondary light is allowed to emit from the emit portion 41b. In this case, phases of the secondary lights emitting from the respective optical fibers are different from each other, and coherence is lowered. In other words, the secondary light is light that emits with a beam divergence angle θ corresponding to Fna of the light guide member 41 and a refractive index n of a light transmission member 57 and has no coherence.

As described above, the light guide member 41 also functions as a light conversion member 53 that generates the secondary light based on the primary light. That is, the light guide member 41 has a light guide function for guiding the primary light and a function of the light conversion member 53.

[Light Conversion Member 53]

The light conversion member 53 itself is omitted.

[Effect]

In this embodiment, since the light guide member 41 also functions as the light conversion member 53, the number of components can be reduced.

Furthermore, in this embodiment, the incident portion 41a of the light guide member 41 is larger than the incident portion 41a in an example where the light guide member 41 is formed of a single optical fiber strand. Therefore, the density of the primary light which enters the optical fiber, per optical fiber is lowered. Thus, according to this embodiment, the density of the secondary light allowed to emit from the emit portion 41b can be lowered, a burden caused due to the secondary light can be prevented from being imposed on a user, and desired safety can be maintained.

Moreover, the present invention is not restricted to the foregoing embodiments as it is, and constituent elements can be modified and embodied in the embodying stage without departing from the gist. Additionally, various inventions can be formed by appropriately combining the constituent elements disclosed in the foregoing embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source apparatus comprising:
   a light source unit that emits primary light;
   an optical illumination unit that converts optical characteristics of the primary light emitted from the light source unit and emits secondary light different from the primary light; and
   an adapter unit that outwardly emits illumination light generated based on the secondary light emitted from the optical illumination unit and that is attachable to/detachable from the optical illumination unit,
   wherein a central axis of the primary light emitted from the light source unit is a light axis,
   in the light axis direction, the optical illumination unit side is a rear side, the adapter unit side is a front side, and a direction orthogonal to the light axis is a lateral side,
   the optical illumination unit comprises:
      a light conversion member that converts the optical characteristics of the primary light and generates the secondary light different from the primary light;
      a secondary light emit portion that is arranged in the front side to the light conversion member and allows the secondary light to emit to the outside of the optical illumination unit; and
      a radiation angle control member that controls a radiation angle of the secondary light allowed to emit to the outside of the optical illumination unit,
   the adapter unit comprises:
      an adapter unit side incident portion which is optically connected to the secondary light emit portion and from which the secondary light allowed to emit from the secondary light emit portion enters; and
      an adapter unit side emit portion that allows the illumination light to emit toward the outside, and
      the radiation angle control member converts a traveling direction of the secondary light so that the secondary light allowed to emit from the light conversion member toward the radiation angle control member in the secondary light allowed to emit from the light conversion member travels toward the adapter unit through the secondary light emit portion;
   wherein a beam divergence angle of the radiation angle control member of the adapter unit is different than a beam divergence angle of the radiation angle control member of the optical illumination unit.

2. The apparatus according to claim 1,
   wherein the optical illumination unit further comprises:
   a primary light incident portion from which the primary light enters and which is smaller than the secondary light emit portion; and
   a holding section that comprises an incident opening portion fitted into the primary light incident portion side, an emit opening portion fitted into the secondary light emit portion side, and a hollow portion continuous from the incident opening portion to the emit opening portion in the light axis direction to hold the primary light incident portion and the secondary light emit portion, and
   the radiation angle control member comprises a reflection member that is arranged on an inner peripheral surface of the holding section and reflects the secondary light toward the secondary light emit portion.

3. The apparatus according to claim 2, wherein the light conversion member is arranged in the hollow portion in such a manner that it is arranged away from the primary light incident portion and ahead of the primary light incident portion.

4. The apparatus according to claim 3,
   wherein the optical illumination unit further comprises a light transmission member that comprises the primary light incident portion and the secondary light emit portion, is arranged between the primary light incident portion and the light conversion member, and arranged to be at least partially continuous from the primary light incident portion to the secondary light emit portion so that the primary light and the secondary light are transmitted there through, the light transmission member is fitted into the hollow portion, and the light conversion member is contained in the light transmission member.

5. The apparatus according to claim 3, wherein the optical illumination unit further comprises a light transmission member that comprises the primary light incident portion, is arranged between the primary light incident portion and the light conversion member, and arranged to be at least partially continuous from the primary light incident portion to the light conversion member so that the primary light and the second light are transmitted there through, the light transmission member is fitted into the hollow portion, and the light conversion member is arranged ahead of the light transmission member and comprises the secondary light emit portion.

6. The apparatus according to claim 4, wherein the optical illumination unit further comprises a light guide member that guides the primary light emitted from the light source unit, the light guide member comprises an emit portion that is optically connected to the primary light incident portion and allows the primary light to emit therefrom, and $$L3 \geq (L2-L1) \times \tan \theta \text{ is achieved,}$$

provided that the center of the emit portion is an origin O, an intersection of the light axis and light conversion member is a point A, an intersection of the light axis and the secondary light emit portion is a point B, the farthest point from the point B in the secondary light emit portion is a point C, an intersection of the light axis and the adapter unit side incident portion is a point D, the farthest point from the point D in the adapter unit side incident portion is a point E, a distance between the origin O and the point A is a distance L, a distance between the origin O and the point B is a distance L2, a distance between the point D and the point E is a distance L3, and an angle formed among the points B, A, and C is an angle θ.

7. The apparatus according to claim 6, wherein each of the light transmission member and the hollow portion has a truncated conical shape whose diameter increases from the rear side toward the front side in the light axis direction.

8. The apparatus according to claim 7, wherein the adapter unit further comprises:

an adapter unit side light conversion member that converts optical characteristics of the secondary light and generates tertiary light different from the secondary light as the illumination light;

an adapter unit side holding section that comprises an adapter unit side incident opening portion fitted into the adapter unit side incident portion side, an adapter unit side emit opening portion fitted into the adapter unit side emit portion side, and an adapter unit side hollow portion continuous from the adapter unit side incident opening portion to the adapter unit side emit opening portion in the light axis direction to hold the adapter unit side incident portion and the adapter unit side emit portion; and an adapter unit side reflection member that is arranged on an inner peripheral surface of the holding section and reflects the secondary light in such a manner that the secondary light travels to the adapter unit side emit portion, the adapter unit side light conversion member is arranged in the adapter unit side hollow portion, and the adapter unit side incident portion is smaller than the adapter unit side emit portion.

9. The apparatus according to claim 6, wherein each of the light transmission member and the hollow portion has a columnar shape.

10. The apparatus according to claim 4, wherein each of the light transmission member and the hollow portion has a parabolic shape, and the light conversion member is arranged in the vicinity of a focal point of a parabola.

11. The apparatus according to claim 10, wherein the adapter unit further comprises:

an adapter unit side light conversion member that converts optical characteristics of the secondary light and generates tertiary light different from the secondary light as the illumination light;

an adapter unit side holding section that comprises an adapter unit side incident opening portion fitted into the adapter unit side incident portion side, an adapter unit side emit opening portion fitted into the adapter unit side emit portion side, and an adapter unit side hollow portion continuous from the adapter unit side incident opening portion to the adapter unit side emit opening portion in the light axis direction to hold the adapter unit side incident portion and the adapter unit side emit portion; and an adapter unit side reflection member that is arranged on an inner peripheral surface of the holding section and reflects the secondary light in such a manner that the secondary light travels to the adapter unit side emit portion, the adapter unit side light conversion member is arranged in the adapter unit side hollow portion, and the adapter unit side incident portion has a size substantially the same as the adapter unit side emit portion.

12. The apparatus according to claim 8 or 11, wherein the adapter unit side light conversion member has the adapter unit side emit portion and is arranged to cover the entire adapter unit side emit opening portion.

13. The apparatus according to claim 12, wherein the light conversion member is formed of at least one of a diffusion member, a spectral conversion member, a light distribution conversion member, a wavelength selection filter, a dimming member, and an optical member, and the adapter unit side light conversion member is formed of at least one of the spectral conversion member, the light distribution conversion member, the wavelength selection filter, the dimming member, and the optical member.

14. The apparatus according to claim 1, wherein the light conversion member also functions as a light guide member that guides the primary light emitted from the light source unit, the light guide member comprises an emit portion that is optically connected to the primary light incident portion and allows the primary light to emit therefrom, the light guide member comprises a bundle fiber formed by bundling optical fiber strands, and the optical fiber has softness and flexibility.

15. The apparatus according to claim 1, wherein the optical illumination unit further comprises a light guide member that guides the primary light emitted from the light source unit, and the light guide member is formed of at least one of a single optical fiber strand, a bundle fiber, a light pipe, and a light wave guide device.

16. The light source apparatus according to claim 1, wherein a front side of the radiation angle control member of the adapter unit is at least a same size as a rear side of the radiation angle control member of the optical illumination unit.

17. The light source apparatus according to claim 1, wherein a front side of the radiation angle control member of the adapter unit is larger than a rear side of the radiation angle control member of the optical illumination unit.

18. The light source apparatus according to claim 1, wherein each of the rear and front sides of the adapter unit has a diameter greater than the front side of the optical illumination unit.

19. The light source apparatus according to claim 1, wherein the adapter unit side emit portion of the adapter unit has a diameter larger than a diameter of the secondary light emit portion of the optical illumination unit.

20. The light source apparatus according to claim 1, wherein a beam divergence angle of the radiation angle control member of the adapter unit is larger than a beam divergence angle of the radiation angle control member of the optical illumination unit.

\* \* \* \* \*